(12) United States Patent (10) Patent No.: US 9,208,564 B2
Degenhardt et al. (45) Date of Patent: Dec. 8, 2015

(54) METHOD AND DEVICE FOR NAVIGATING AN ENDOSCOPIC CAPSULE

(75) Inventors: Achim Degenhardt, Erlangen (DE); Clemens Jungkunz, Erlangen (DE); Rainer Kuth, Höchstadt (DE)

(73) Assignee: Siemens Aktiengesellschaft, Munich (DE)

( * ) Notice: Subject to any disclaimer, the term of this patent is extended or adjusted under 35 U.S.C. 154(b) by 311 days.

(21) Appl. No.: 13/202,903

(22) PCT Filed: Nov. 30, 2009

(86) PCT No.: PCT/EP2009/066028
§ 371 (c)(1),
(2), (4) Date: Aug. 23, 2011

(87) PCT Pub. No.: WO2010/099841
PCT Pub. Date: Sep. 10, 2010

(65) Prior Publication Data
US 2011/0304717 A1 Dec. 15, 2011

(30) Foreign Application Priority Data
Mar. 5, 2009 (DE) .......... 10 2009 011 831

(51) Int. Cl.
A61B 17/22 (2006.01)
G06T 7/00 (2006.01)
A61B 1/00 (2006.01)
A61B 1/04 (2006.01)
A61B 19/00 (2006.01)

(52) U.S. Cl.
CPC .......... *G06T 7/0042* (2013.01); *A61B 1/00158* (2013.01); *A61B 1/041* (2013.01); *A61B 19/5244* (2013.01); *A61B 2019/2253* (2013.01); *A61B 2019/5251* (2013.01); *A61B 2019/5289* (2013.01); *G06T 2207/10016* (2013.01); *G06T 2207/10068* (2013.01); *G06T 2207/30028* (2013.01)

(58) Field of Classification Search
CPC ....................................................... H04N 7/18
USPC ............................................................ 348/65
See application file for complete search history.

(56) References Cited

U.S. PATENT DOCUMENTS 7,200,253 B2 * 4/2007 Glukhovsky et al. ......... 382/128
7,675,394 B2 * 3/2010 Fujimori et al. .............. 335/151
7,794,396 B2 * 9/2010 Gattani et al. ................ 600/173

(Continued)

FOREIGN PATENT DOCUMENTS

DE 102005032577 A1 1/2005
JP 06030896 2/1994

(Continued)

*Primary Examiner* — Dave Czekaj
*Assistant Examiner* — Kehinde O Abimbola
(74) *Attorney, Agent, or Firm* — Schiff Hardin LLP

(57) ABSTRACT

In a method and system for navigating an endoscopy capsule in a patient, wherein the endoscopy capsule includes a camera, a first image of an object in the interior of the patient is obtained with the camera, in which a re-identifiable structural feature of the object is identified. Successive images of the interior of the patient are then automatically obtained with the camera, and the endoscopy capsule is controlled, for each image, so that the position of the structural feature remains unchanged in the individual images while the image scale is intentionally enlarged or reduced.

12 Claims, 2 Drawing Sheets

(56) References Cited

U.S. PATENT DOCUMENTS

| | | |
|---|---|---|
| 2003/0060702 A1 | 3/2003 | Kuth et al. |
| 2005/0281446 A1* | 12/2005 | Glukhovsky et al. ......... 382/128 |
| 2007/0021654 A1* | 1/2007 | Preidel et al. ................. 600/160 |
| 2007/0171012 A1* | 7/2007 | Fujimori et al. ............... 335/151 |
| 2007/0171013 A1* | 7/2007 | Fujimori et al. ............... 335/151 |
| 2007/0221233 A1 | 9/2007 | Kawano et al. |
| 2007/0238987 A1 | 10/2007 | Minai et al. |
| 2008/0027329 A1* | 1/2008 | Glukhovsky ................. 600/476 |
| 2008/0036856 A1* | 2/2008 | Yamada et al. ................. 348/72 |
| 2008/0108873 A1* | 5/2008 | Gattani et al. ................ 600/168 |
| 2008/0119691 A1 | 5/2008 | Yagi et al. |
| 2008/0249359 A1* | 10/2008 | Abraham-Fuchs et al. .. 600/117 |
| 2008/0312501 A1* | 12/2008 | Hasegawa et al. ............ 600/117 |
| 2009/0043157 A1* | 2/2009 | Hirakawa et al. ............. 600/109 |
| 2009/0253954 A1* | 10/2009 | Katayama ..................... 600/103 |
| 2009/0312618 A1* | 12/2009 | Hengerer et al. ............. 600/345 |
| 2010/0056866 A1 | 3/2010 | Uchiyama et al. |
| 2011/0098532 A1* | 4/2011 | Graumann et al. ........... 600/117 |

FOREIGN PATENT DOCUMENTS

| | | |
|---|---|---|
| JP | 09266882 | 10/1997 |
| JP | 10309256 | 11/1998 |
| JP | 10314104 | 12/1998 |
| WO | WO2006/045011 A2 | 4/2006 |

* cited by examiner

METHOD AND DEVICE FOR NAVIGATING AN ENDOSCOPIC CAPSULE

BACKGROUND OF THE INVENTION

1. Field of the Invention

The invention concerns a method and a device for navigation of an endoscopy capsule.

2. Description of the Prior Art

An endoscopy capsule of a general type is known from DE 101 42 253, for example. This conventional endoscopy capsule contains at least one camera that sends up-to-date images or a live video image. Such capsules can include different inspection, diagnosis or therapy devices. For example, this can be a video camera, a biopsy pincer, a clip or a pharmaceutical reservoir. The capsule furthermore contains a magnetizable or permanent magnet element which the capsule is moved wirelessly in the patient. For this purpose, the patient is situated wholly or partially in an electrical coil system composed of multiple (14, for example) individual coils. Suitable magnetic fields or, respectively, gradient magnetic fields are generated by the coil system, which magnetic fields or gradient magnetic fields generate forces or, respectively, torques at the capsule, namely at the magnetic element located in the patient. The capsule in the patient thus can be specifically moved in arbitrary directions. Areas of use are primarily hollow organs, in particular the human gastrointestinal tract (for example) that can be traversed in its entirety with the capsule in a single pass.

The aforementioned complete system or examination method is also called MGCE (magnetically guided capsule endoscopy). In a first generation of these apparatuses or capsules, the respective spatial location of the capsule in the coil system or relative to the coil system is not known, since the system does not possess an expensive and elaborate positioning system. The user, who manually controls the capsule by operating the system, therefore cannot see or locate the capsule extracorporeally.

In principle, such a capsule in the patient could easily be made visible with the aid of x-rays or fluoroscopy, but the x-ray exposure to the patient and the costs for a corresponding system expansion are counter-considerations. Accordingly, the user must orient himself or herself in the patient solely by using the images delivered by the capsule or an additional endoscope introduced into the patient in order to be able to control the capsule in a desired direction or at a desired location in the patient.

Only the current solid angle or the orientation of the longitudinal axis of the capsule in space or the coil system can be set from the outside, thus by the coil system. The desired direction is namely applied by a homogeneous magnetic field. The capsule aligns with its middle longitudinal axis corresponding to this homogeneous magnetic field. However, given a parallel alignment of magnetic moment of the capsule and external magnetic field the force on the capsule due to the corresponding cross-product is zero. It consequently takes a certain period of time until the capsule becomes aligned in this desired direction of the homogeneous magnetic field. Moreover, since the capsule floats in fluid (for example in the stomach), an oscillation of the capsule or a temporal deviation from the desired spatial direction can occur due to sloshing of the fluid, for instance as a result of peristalsis, heartbeat or breathing movements, since the capsule is held in this direction only by small forces.

The control and navigation of an endoscopy capsule in a patient without the aforementioned absolute knowledge of the precise capsule location in the system is thus not achieved in a satisfactory manner in conventional systems.

SUMMARY OF THE INVENTION

An object of the invention is to provide an improved method and a device to navigate an endoscopy capsule in a patient.

The invention is based on the insight that the goal or spirit and purpose of a navigation of the capsule is always a desired guidance of the capsule toward a marked conspicuity in the patient that, for example, should be examined or treated. Such a conspicuity is, for example, a lesion, an organ outlet, a defined organ structure or the like. In particular, a close-up exposure of the conspicuity with high optical resolution and an overview exposure of the same with its surroundings is generally desired with the use of the capsule or its camera. For the latter exposure the capsule is then to be distanced a bit from the corresponding subject. The basis of the invention is to automate the alignment of the capsule with respect to the approach to or distancing from a target subject (the conspicuity).

According to the invention, a first image of a subject inside the patient is initially acquired with the camera contained in the endoscopy capsule. The subject is, for example, an inner wall of the organ of the patient in which the capsule is presently located, for instance the stomach or its wall. A re-identifiable structure feature of the subject is then identified in the image. To be re-identified relative to its environment, the structure feature must have characteristics, for example color differences, edges, clear boundaries, a characteristic shape or the like in order to be able to re-identify it in the current image and also later images produced from the same region of the subject. Ideally the aforementioned conspicuity in the patient that is the target of the navigation of the capsule is selected as a structure feature.

In the further course of the method images of the inside of the patient are automatically acquired continuously. The time interval between two exposures is selected using the inertia of the capsule movement, for example, so that the alignment of the capsule cannot change so far that the structure feature could be removed from the imaging region of the camera. The structure feature is then automatically sought in the image for each of the newly acquired images.

The endoscopy capsule is then controlled so that the position of the structure feature in the image remains unchanged while the imaging scale is specifically enlarged or reduced in size. In other words, for this purpose, the distance of the capsule relative to the subject is then reduced in size or increased so that the subject in the image is smaller or larger (a rigid optic of the camera is normally assumed). The control is implemented independent of or, respectively, counter to or, respectively, directly for compensation of disruptive forces that, for example, want to move the capsule sideways.

In other words, with the method it is ensured that the structure feature is optimally held at the same relative location in the image, regardless of at what distance or viewing angle the capsule is located relative to the structure feature. The capsule or the camera thereof thus always remains aligned on the structure feature.

With the method according to the invention a semi-automatic navigation is provided to the user using image contents, namely the structure feature. The alignment of the capsule is automated; the user needs only to specifically monitor the displacement of the capsule. One of the most frequent objects of capsule navigation in endoscopy—namely the acquisition of high-resolution, local photos as well as overview exposures of structure features—is therefore simplified.

In an embodiment of the method, in the first image at least two predeterminable directions leading from the structure feature to the edge are selected. These directions are established only once in the first image and maintained for the additional method. The endoscopy capsule is then additionally controlled so that the relationship of the imaging scales of the images following the first image are kept constant or are specifically influenced in the respective directions. The capsule is thus either held at a desired angle in front of the subject (in other words the capsule is held at the same solid angle on a spherical shell around the subject) or the angle relative to the subject is specifically affected. In other words, the capsule is moved around the subject on the spherical shell. The directions are selected so that the imaging scales necessarily change given a variation of the alignment of the camera on the subject or a distance change relative to the subject.

In one variant of this embodiment the distances between structure feature and edge of the image are automatically determined in the selected directions. A first relationship of the measured distances relative to one another is now determined. In the case of multiple distances, these are multiple relationships. The directions are selected so that, given a change of the alignment of the camera on the subject or the distance change from the object, the relationships of the distances that are determined above necessarily change. The distances in the established, predetermined directions and their current relationship to one another are then also determined automatically in the following images.

Given a deviation of the current relationship from the first relationship, the position of the endoscopy capsule is then corrected automatically. The correction takes place in a suitable direction so that the expected relationship of the distances in the next image to be acquired again approximates the first relationship. In other words, according to the invention the relative truncations in different directions between the structure feature and the image edge in successively acquired images are evaluated, and the capsule is controlled by means of a control loop so that these relative truncations are kept constant or in the same relationship.

As mentioned above, in a preferred embodiment of the method a lesion of interest in a patient is identified as a structure feature. As mentioned, the observation, imaging or examination of lesions is one of the paramount tasks in capsule endoscopy.

Two variants exist for the first identification of the structure feature in the first acquired image. In one embodiment of the method the structure feature is identified by a user. The experience of the user can hereby be advantageous in the selection of the structure feature since said user deliberately selects the subject of his interest in the form of the structure feature as a relative fixed point.

However, in an alternative embodiment of the method the structure feature is sought automatically. The user thus can be relieved of the identification of conspicuous lesions with the assistance of image processing methods or methods of artificial intelligence, which means an additional facilitation for the user.

In a further embodiment of the method, in addition to the aforementioned automatic alignment relative to the structure feature, the endoscopy capsule is moved toward or away from the feature. A semi-automatic movement—thus a movement stabilized relative to its direction—toward the structure or away from the results. The production of the detail exposure and overview exposure of the structure feature that are addressed above is thus particularly facilitated.

In an advantageous embodiment of these variants, the endoscopy capsule is automatically moved toward the subject or the structure until it strikes the subject. For example, an automatic approach of the structure feature takes place for the purpose of taking a biopsy, in particular when this has been optimally placed in the center of the first image.

Overall, according to the invention automated maneuvers such as "reverse without changing the viewpoint", "approach a selectable point in the field of view" result with the cited embodiments. The movements can either be implemented automatically until impact or interactively by the user with forwards or backwards movements. The selectable point, viewpoint, etc. can be freely established by the selection of an arbitrary structure feature present in the image, which structure feature must not be a pathological conspicuity of the patient.

In an alternative embodiment of the method, in addition to the aforementioned automatic alignment at a constant distance—thus on a spherical surface—the capsule is moved around the structure feature. In this method variant the distance of the capsule from the subject is thus kept constant, and only the viewing angle on the subject is varied. In particular, three-dimensional structure features projecting from the subject or recessed into this can be imaged particularly simply from different directions. This variant thus yields an additional automatic maneuver: "change the viewing angle without changing the viewpoint", meaning that the structure feature remains at the same relative position in the image, for example in the image center, and only the viewing direction changes.

The above object also is achieved by a device according to the invention that, in addition to the endoscopy capsule with a camera, includes a control and evaluation unit with a program implemented in this to execute the method explained above in various embodiments among the cited embodiments.

In an embodiment, the device contains an input unit that can be operated by the user. The aforementioned embodiments of the method that require a user input can also be implemented, for example for identification of the structure feature.

DESCRIPTION OF THE PREFERRED EMBODIMENTS

Figure 1:
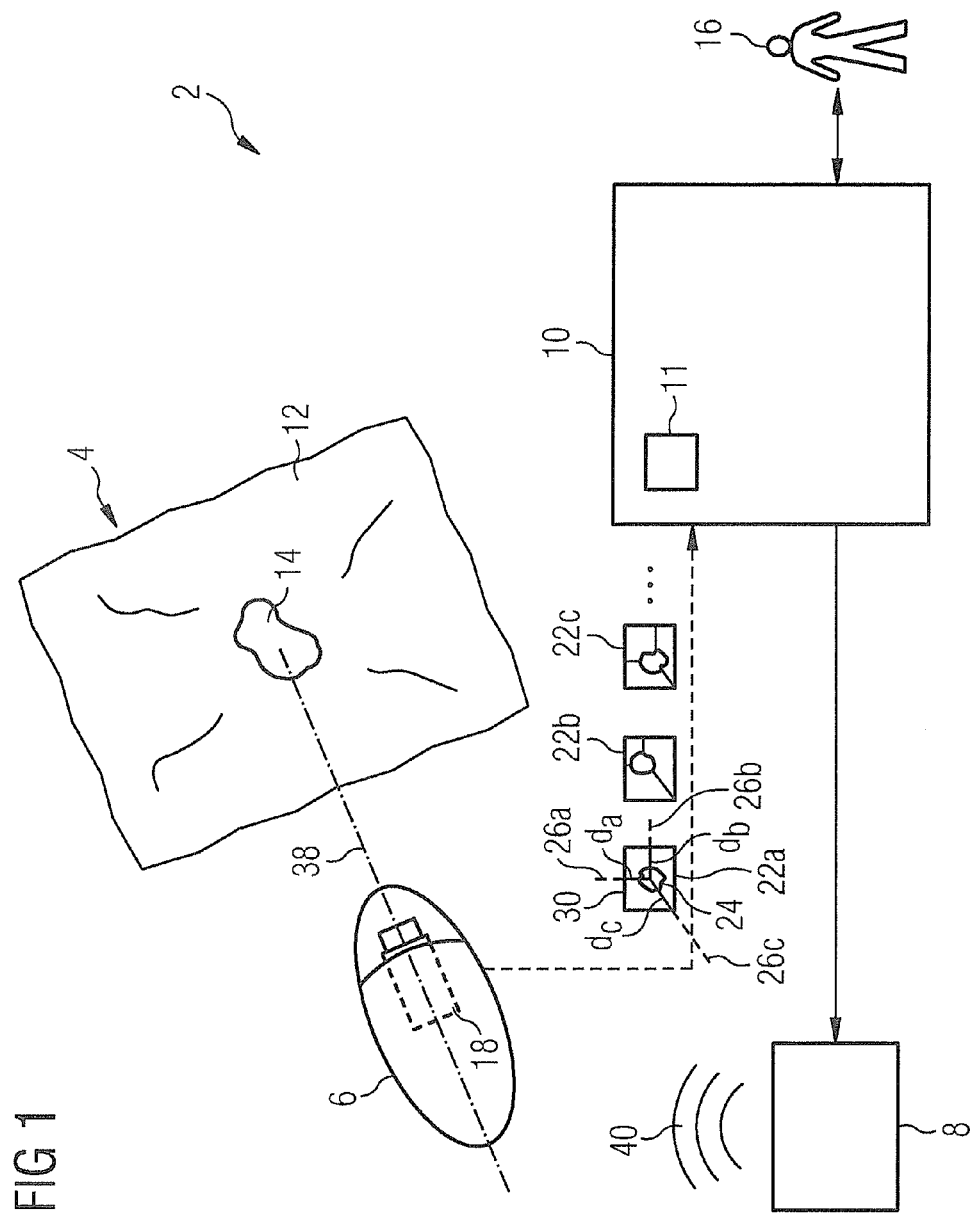
FIG. 1 schematically illustrates an MGCE system according to the present invention, in operation.

FIG. 1 shows an MGCE system 2 with which a patient 4 is examined directly. Of the patient 4, only a subject 12 inside said patient 4 is shown, namely the stomach wall. A lesion 14 is located at the stomach wall. The MGCE system 2 includes an endoscopy capsule 6 introduced into the patient 4, a magnetic coil system 8 to exert force without contact on the endoscopy capsule 6, and a control and evaluation unit 10 with a program 11 controlling the workflows described below.

The endoscopy capsule 6 was already passed into the stomach of the patient 4 by a user 16 via manual control at an input unit 17 of the control and evaluation unit 10. For this the user 16 used images (in the form of a live video image) delivered from the camera 18 installed in the endoscopy capsule 6.

Figure 2:
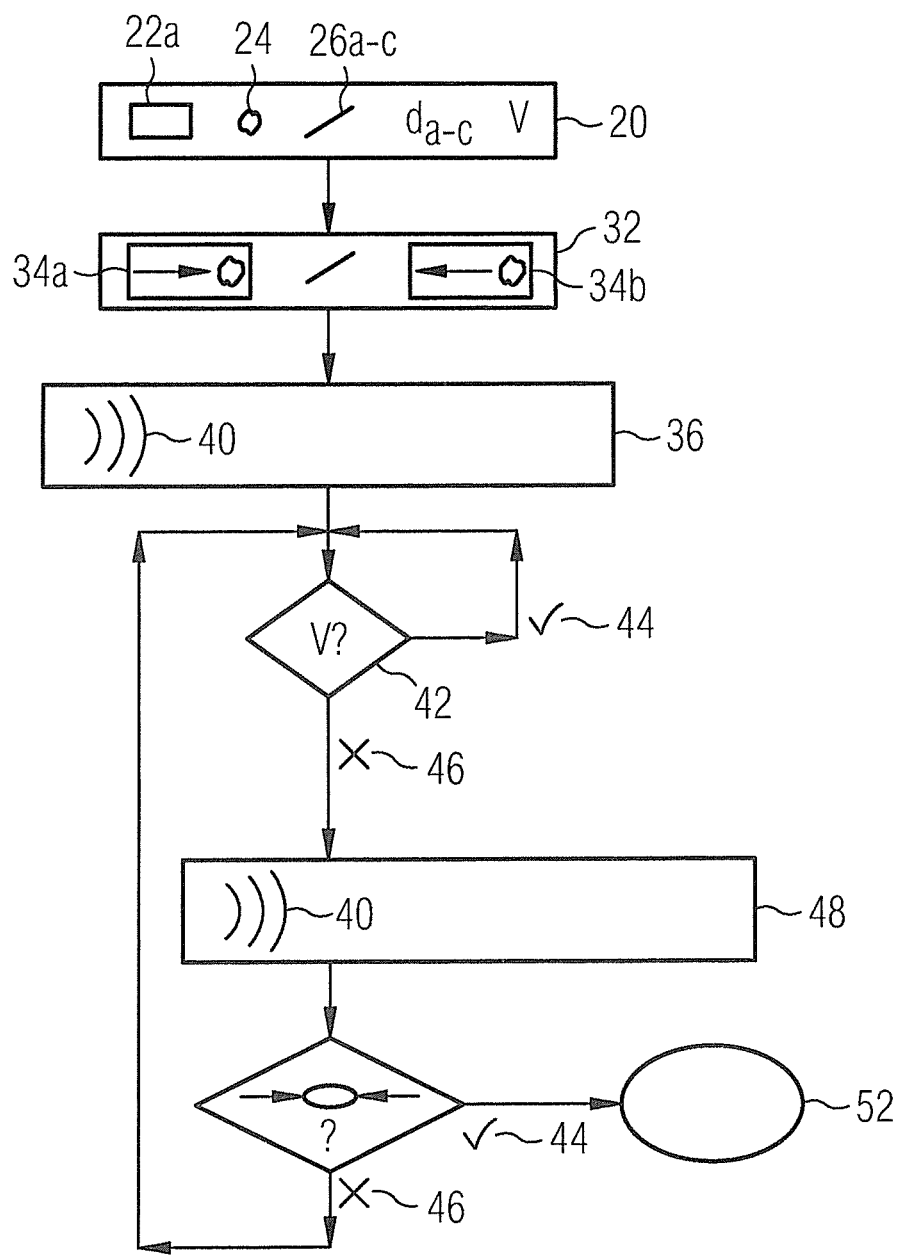
FIG. 2 is a flowchart for semi-automatic navigation of the endoscopy capsule shown in FIG. 1, in accordance with the present invention.

Since the user 16 considers the lesion 14 as a structure of interest to him, at the control and evaluation unit 10 he starts the automatic method according to the invention according to the program 11, which method is shown in FIG. 2.

In a first Step 20 the camera 18 takes a first image 22a which depicts the lesion 14. In the image 22a the user 16 identifies the lesion 14 as a structure feature 24. In an alternative embodiment, this is implemented automatically by the program 11 itself with the aid of an image processing.

Three directions 26a-c are now predetermined which point from the structure feature 24 to the edge 30 of the image. According to two embodiments this is also performed again by the user 16 or automatically by the program 11. The respective distances $d_{a-c}$ between structure feature 24 and edge 30 are now defined automatically by the program 11. Moreover, the first relationships $V_{11}=d_a/d_b$ and $V_{12}=d_b/d_c$ are defined.

In a next Step 32 the user 16 gives the command "approach the structure feature" as a command 34a. In an alternative embodiment of the method, the user gives the command 34b as "distance from the structure feature". The following then takes place.

In a further Step 36 the control and evaluation unit 10 gives commands to the magnetic coil system 8 for the application of field gradients in the view direction of the camera 18 in order to exert a force on the endoscopy capsule 6. The magnetic coil system 8 generates corresponding fields 40. Strength and direction of the required fields 40 are determined with optimal precision by the control and evaluation unit 10 according to a current position (roughly estimated from the previous control history) and alignment of the capsule. Among other things, gravity and the current buoyancy which the capsule experiences experimentally or in a known manner in the patient 4 are taken into account in the application of the fields 40.

An actual movement of the endoscopy capsule 6 takes place via the fields 40. The camera 18 now continuously delivers images 22b, 22c etc. Since the exact attitude of the endoscopy capsule 6 in the patient 4 is known neither to the user 16 nor the MGCE system 2, the application of the fields 40 (which are initially roughly estimated) leads to a movement of the capsule 6 in one direction which, under the circumstances, does not run precisely in the desired direction, namely in the direction of the lesion 14. Although the image of the lesion 14 is larger, it therefore migrates to a different location in the image 22b.

In a decision Step 42 the image 22b is evaluated automatically in that the structure feature 24 is automatically re-identified or, respectively, relocated again in the form of the image of the lesion 14. In the directions 26a-c that are now firmly selected, the current distances $d_{a-c}$ are now determined and current relationships $V_{21,22}$ corresponding to these are formed. The current relationships $V_{21,22}$ are now compared with the previously calculated relationships $V_{11,12}$. If the current relationships have remained identical to the first relationships, no variation of the fields 40 takes place according to a yes Step 44.

Since a deviation has occurred in the present case, in a no Step 46 the control and evaluation unit 10 determines corrected fields 40 in order to deflect the endoscopy capsule 6 more precisely in the direction of the lesion 14. The no Step 46 thus leads to the correction of gradient and flow direction of the fields 40 counter to the deviation of the structure feature 24 that can be recognized in the image 22b. In other words, the position of the endoscopy capsule is automatically corrected in one direction so that the relationship $V_{31,32}$ that is to be expected again approximates the first relationship $V_{11,12}$ in the next image 22c to be acquired.

The same also applies for the case that the capsule 6 should remain at the current location, and therefore no fields 40 are currently generated but said capsule 6 is rotated slightly by peristalsis of the patient 4. The current relationships $V_{21,22}$ then also change and a corresponding correction by fields 40 is suggested.

In a query step 50 an input of the user 16 is queried as to whether said user 16 would like to end the movement of the endoscopy capsule 6 in the yes Step 44, which leads to the end 52 of the method. If not, a no Step 46 continues the selected command 34a or 34b, which again leads to the decision Step 42, i.e. the acquisition of additional images 22c etc., determination of the distances $d_{a,b}$ etc.

Although modifications and changes may be suggested by those skilled in the art, it is the intention of the inventors to embody within the patent warranted heron all changes and modifications as reasonably and properly come within the scope of their contribution to the art.

We claim as our invention:

1. A method to navigate an endoscopy capsule in a patient, comprising:

with a magnetic field generated by an extracorporeal magnetic guidance system, magnetically guiding an endoscopy capsule, having a longitudinal axis and containing a single camera, intracorporeally in a patient in an environment in the patient that subjects said endoscopy capsule to movement, caused by said environment, that continually displaces said longitudinal axis;

while said endoscopy capsule is in said environment in the patient and thus while said longitudinal axis is being continually displaced, using the single camera to acquire a first image of an interior of the patient within a field of view of said single camera;

providing said first image to a computerized processor and, in said processor, identifying a structural feature of the interior of the patient, that is represented in said first image with said longitudinal axis intersecting said structural feature, said structural feature having at least one feature characteristic that allows said structural feature to be re-identified in images obtained subsequently to said first image;

in said processor, automatically determining a spatial relationship of said structural feature represented in said first image with respect to another item in said first image that is located at a distance in said first image from said structural feature;

after acquiring said first image, automatically acquiring a plurality of additional images of the interior of the subject with said single camera while said endoscopy capsule is in said environment and thus while said longitudinal axis is being continually displaced, with said endoscopy capsule being located at respectively different distances from said structural feature at respective times of acquisition of said additional images;

providing said additional images to said processor and, in said processor, automatically determining said spatial relationship of said structural feature represented in each of the additional images to said item in each of said additional images;

in said processor, automatically scaling the spatial relationship determined in each of the additional images with respect to the distance from the structural feature from which each of said additional images was acquired;

in said processor, generating a control signal for said extracorporeal magnetic guidance system that maintains said spatial relationship unchanged in each of said additional images dependent on the respective scale of each of said additional images, and that thereby maintains said longitudinal axis intersecting said structural feature despite said continual displacement of said longitudinal axis by said movement caused by said environment; and supplying said control signal from said processor to said extracorporeal magnetic guidance system and, in said extracorporeal magnetic guidance system, using said control signal to adjust said magnetic field to guide said endoscopy capsule during acquisition of said additional images with said structural feature always in said field of view of said single camera because said longitudinal axis is maintained intersecting said structural feature.

2. A method as claimed in claim 1 comprising, in said processor:

identifying and using an edge of the image as said item that is located at a distance in said image from said structural feature;

in each of said additional images, selecting at least two directions leading from the structural feature in each image to said edge of each image, said structural feature exhibiting respective distances to said edge along respectively along said at least two directions; and generating said control signal to maintain said position of said structural feature in each of said additional images unchanged by maintaining a relationship of the respective distances along said respective directions constant or at a predetermined relationship in each of said additional images.

3. A method as claimed in claim 2 comprising, in said processor:

in said first image, automatically determining at least two distances between the structural feature and said edge of said first image, along said respective directions, and automatically determining a first relationship of said distances with respect to each other;

in each of said additional images, determining said distances along said directions and identifying a relationship of said distances and directions in each of said additional images, as a current relationship; and upon deviation of said current relationship from said first relationship, automatically modifying said control signal to cause the extracorporeal magnetic guidance system adjust said magnetic field to correct a position of the endoscopy capsule in one of said directions to cause said current relationship in a next additional image to approximate said first relationship.

4. A method as claimed in claim 1 comprising identifying a lesion in the body of the patient as said structural feature.

5. A method as claimed in claim 1 comprising providing said first image to said processor by transmitting said first image to said processor extracorporeally of the patient and displaying said first image at an extracorporeal display in communication with said processor, and identifying said structural feature in said first image by manual user interaction with an extracorporeal display of said first image and thereafter manually entering a designation of said structural feature into said processor.

6. A method as claimed in claim 1 comprising automatically identifying said structural feature in said processor by applying a pattern recognition algorithm to said first image.

7. A method as claimed in claim 1 comprising moving said endoscopy capsule toward or away from said structural feature with said magnetic guidance system.

8. A method as claimed in claim 6 comprising moving said endoscopy capsule automatically toward said structural feature in the body of the subject with said extracorporeal magnetic guidance system until said endoscopy capsule strikes the structural feature in the body of the subject.

9. A method as claimed in claim 1 comprising moving said endoscopy capsule at a constant distance around the structural feature in the body of the subject with said extracorporeal magnetic guidance system.

10. An endoscopy system comprising:

an endoscopy capsule having a longitudinal axis and containing a single camera;

an extracorporeal magnetic guidance system configured to generate a magnetic field that magnetically guides the endoscopy capsule containing the single camera intracorporeally in a patient in an environment in the patient that subjects said endoscopy capsule to movement, caused by said environment, that continually displaces said longitudinal axis;

said single camera being configured to acquire a first image of an interior of the patient within a field of view of said single camera while said endoscopy capsule is in said environment in the patient and thus while said longitudinal axis is being continually displaced;

a computerized processor provided with said first image, said processor being configured to identify a structural feature of the interior of the patient, that is represented in said first image with said longitudinal axis intersecting said structural feature, said structural feature having at least one feature characteristic that allows said structural feature to be re-identified in images obtained subsequently to said first image;

said processor being configured to automatically determine a spatial relationship of said structural feature represented in said first image with respect to another item in said first image that is located at a distance in said first image from said structural feature;

said single camera being configured, after acquiring said first image, to automatically acquire a plurality of additional images of the interior of the subject with said camera while said endoscopy capsule is in said environment and thus while said longitudinal axis is being continually displaced, with said endoscopy capsule being located at respectively different distances from said structural feature at respective times of acquisition of said additional images;

said processor being provided with said additional images and being configured to automatically determine said spatial relationship of said structural feature represented in each of the additional images to said item in each of said additional images;

said processor being configured to automatically scale the spatial relationship determined in each of the additional images with respect to the distance from the structural feature from which each of said additional images was acquired;

said processor being configured to generate a control signal for said extracorporeal magnetic guidance system that maintains said spatial relationship unchanged in each of said additional images dependent on the respective scale of each of said additional images, and that thereby maintains said longitudinal axis intersecting said structural feature despite said continual displacement of said longitudinal axis by said movement caused by said environment; and said processor being configured to supply said control signal from said processor to said extracorporeal magnetic guidance system and said extracorporeal magnetic guidance system being configured use said control signal to adjust said magnetic field to guide said endoscopy capsule during acquisition of said additional images with said structural feature always in said field of view of said single camera because said longitudinal axis is maintained intersecting said structural feature.

11. An endoscopy system as claimed in claim 10 wherein said processor is configured to:
   identify and use an edge of the image as said item that is located at a distance in said image from said structural feature;
   in each of said additional images, select at least two directions leading from the structural feature in each image to said edge of each image, said structural feature exhibiting respective distances to said edge along respectively along said at least two directions; and
   generate said control signal to cause said extracorporeal magnetic guidance system to adjust said magnetic field control said movement and positioning of said endoscopy capsule to maintain said position of said structural feature in each of said additional images unchanged by maintaining a relationship of the respective distances along said respective directions constant or at a predetermined relationship in each of said additional images.

12. A system as claimed in claim 11 wherein said processor is configured to:
   in said first image, automatically determine at least two distances between the structural feature and said edge of said first image, along said respective directions, and automatically determining a first relationship of said distances with respect to each other;
   in each of said additional images, determine said distances along said directions and identifying a relationship of said distances and directions in each of said additional images, as a current relationship; and
   upon deviation of said current relationship from said first relationship, modify said control signal to cause the magnetic guidance system to adjust said magnetic field to correct a position of the endoscopy capsule in one of said directions to cause said current relationship in a next additional image to approximate said first relationship.

\* \* \* \* \*